United States Patent [19]
Wong et al.

[11] Patent Number: 5,861,278
[45] Date of Patent: Jan. 19, 1999

[54] HNF3δ COMPOSITIONS

[75] Inventors: Gordon W. Wong, Brookline; Kwok-Ming Yao, Waltham, both of Mass.

[73] Assignee: Genetics Institute, Inc., Cambridge, Mass.

[21] Appl. No.: 742,753

[22] Filed: Nov. 1, 1996

[51] Int. Cl.$^6$ .............................. C12P 21/06; C12N 1/00; C12N 5/10; C12N 15/12; C12N 15/63

[52] U.S. Cl. ...................... 435/69.1; 435/243; 435/320.1; 435/325; 435/410; 536/23.1; 536/23.5

[58] Field of Search ................................. 435/320.1, 325, 435/410, 243, 69.1; 536/23.5, 23.1

[56] References Cited

PUBLICATIONS

Weigel et al., Cell 57:645–658 (1989).
Weigel and Jackle, Cell 63:455–456 (1990).
Costa, Liver and Gene Expression (Tronche and Yaniv, eds.), pp. 183–204 (R. G. Landes Company) (1994).
Lai et al., PNAS USA 90:10421–10423 (1993).
Kaufman et al., Nucl. Acids Res 19:4485–4490 (1991).
Ngo et al., The Protein Folding Problem and Tertiary Structure Prediction, Mertz et al (eds.), pp. 433 and 492–495, Birkhauser, Boston 1994.
Westendorf et al., PNAS USA, vol. 91, pp. 714–718, Jan. 1994.

*Primary Examiner*—Terry A. McKelvey
*Attorney, Agent, or Firm*—Steven R. Lazar

[57] ABSTRACT

Purified HNF3δ proteins and processes for producing them are disclosed. DNA molecules encoding the HNF3δ proteins are also disclosed. The proteins may be used in regulating the transcription of one or more genes involved in the formation, differentiation, proliferation and maintenance of cells which form organ tissues, particularly pancreatic cells, as well as other tissue repair.

18 Claims, No Drawings

HNF3δ COMPOSITIONS

The present invention relates to a novel family of purified proteins designated Hepatocyte Nuclear Factors-3 (HNF3), DNA encoding them, and processes for obtaining them. These proteins may be used to induce changes in the transcription and expression of factors in tissue, organs, and particularly, in pancreatic tissue. Thus, these proteins may be useful in the treatment of pancreatic disorder, and in the enhancement and/or inhibition of cellular formation, growth, differentiation, proliferation and/or maintenance, for example formation of pancreatic tissue. These proteins may also be used for augmenting the activity of other tissue regenerating factors. In particular, the present invention relates to the isolation of a new protein in the HNF3 family of proteins. This novel protein, and the gene encoding it are designated as HNF3δ.

BACKGROUND OF THE INVENTION

The search for the molecule or molecules responsible for the formation, proliferation, differentiation and maintenance of tissue and organs, such as the pancreas, has been extensive. The structures of several proteins in the family designated as Hepatocyte Nuclear Factors-3/Forkhead or HFH, have previously been elucidated. Weigel et al., *Cell*, 57: 645–658 (1989); Weigel and Jackle, *Cell*, 63: 455–456 (1990). The HNF3 branch of the HFH family, HNF3α, -3α, and -3γ, were originally identified in hepatocytes, and were hypothesized to be liver transcription factors which bind to recognition sites in DNA regulatory regions. Costa, in *Liver Gene Expression*, (Tronche and Yaniv, eds.) at pp. 183–204 (R. G. Landes Company)(1994). It was further observed that binding of different combinations of liver factors provided varied promoter control while minimizing the requisite number of regulatory proteins. Thus, the HNF3 family may be capable of regulating the transcription of multiple proteins. During gastrulation of mouse embryos, murine HNF3β and -3α were observed to be expressed during early and late primitive streak stages of gastrulation, respectively. Later in development, all three known HNF3 genes (HNF3α, -3β, and -3γ) were expressed in the gut, pancreas and liver primordium, while only HNF3α, and -3β were expressed in lung. All three HNF3 genes were co-expressed in parenchymal hepatocyte cells, and in HepG2, H4IIE and FTO-2B hepatoma cell lines. HNF3α and -3β were found to be expressed in the lung and in lower amounts in the intestine, whereas HNF3γ MRNA is transcribed in the testis but not in sertoli cells. HNF3β protein is also expressed in the pancreas, where it recognizes a HNF3 binding site required for transcriptional activation by the α-amylase enhancer region. The HNF3α gene is abundantly transcribed within a thin epithelial cell layer lining the pulmonary bronchioles, suggesting that it may regulate the transcription of genes whose protein products are secreted into the lung airway. HNF3β is absent from the bronchiolar epithelium, but expressed at high levels in the smooth muscle surrounding bronchioles and arterioles, suggesting that the HNF3 genes may regulate different target genes. The HNF3 proteins have been shown to collaborate with other liver transcription factors to regulate the expression of over a dozen liver genes, including serum carrier proteins, pharmacologically active polypeptides and genes encoding enzymes involved in glucose metabolism. Thus, the HNF3 proteins are capable of regulating a large number of genes with differing effects. Lai et al., *PNAS USA* 90: 10421–10423 (1993) found that HNF3α and HNF3β showed an inhibitory effect in cells of pancreatic origin on the promoter of the glucagon gene. Thus, the HNF3 proteins are capable of regulating genes present in pancreatic cells.

SUMMARY OF THE INVENTION

The present invention provides additional novel members of the HNF3 family of proteins, which the present inventors have named HNF3δ. The HNF3δ proteins of the present invention show similarities in structure and function to known member of the HNF3 family. However, they are also potentially distinct in their localization and binding recognition sites. For this reason, the HNF3δ proteins, DNA sequences encoding them and methods of using the protein and DNA sequences represent an important new invention.

In certain embodiments, the present invention provides for an isolated polynucleotide comprising a nucleotide sequence selected from the group consisting of:

(a) the nucleotide sequence of SEQ ID NO: 1 from nucleotide 1 or 88 to nucleotide 2400 or 3441; or SEQ ID NO: 3 from nucleotide 1 or 70 to 2358 or 3342;

(b) a nucleotide sequence capable of hybridizing to a nucleic acid sequence specified in (a);

(c) a nucleotide sequence encoding the amino acid sequence of SEQ ID NO:2 or SEQ ID NO: 4 and varying from the sequence of the nucleotide sequence specified in (a) as a result of degeneracy of the genetic code;

(d) a nucleotide sequence comprising a fragment of (a) which encodes an amino acid sequence comprising nucleotides 88 to 2400 or 3441 of SEQ ID NO: 1 or a DNA sequence comprising nucleotides 70 to 2358 or 3342 of SEQ ID NO: 3;

(e) a nucleotide sequence comprising a fragment of (a) which encodes an amino acid sequence comprising amino acids 1 to 771 of SEQ ID NO: 2; or amino acid sequence comprising amino acids 1 to 763 of SEQ ID NO: 4; and (f) an allelic variant of the nucleotide sequence specified in (a). In preferred embodiments, the nucleotide sequence encodes for a protein having HNF3δ activity. In other embodiments, the nucleotide sequence is operably linked to an expression control sequence.

The invention also provides for a host cell transformed with such polynucleotides, including mammalian cells. A process is also provided for producing an HNF3δ protein, said process comprising: (a) growing a culture of the host cell of the invention in a suitable culture medium; and (b) purifying the HNF3δ protein from the culture. Proteins produced according to such processes are also provided.

Pharmaceutical compositions are also provided comprising such polynucleotides and a pharmaceutically acceptable carrier. In preferred embodiments, the polynucleotide is contained in a vector suitable for gene therapy and/or the composition further comprises agents capable of increasing the uptake of said polynucleotide by cells.

The invention further provides an isolated HNF3δ protein comprising an amino acid sequence selected from the group consisting of:

(a) the amino acid sequence of SEQ ID NO: 2; or SEQ ID NO: 4

(b) fragments of (a) having HNF3δ activity.

Preferred embodiments include proteins comprising the amino acid sequence of SEQ ID NO: 2 or SEQ ID NO: 4, proteins comprising amino acids 1 to 771 of SEQ ID NO: 2; and proteins comprising amino acids 1 to 763 of SEQ ID NO: 4. Pharmaceutical compositions comprising such proteins and a pharmaceutically acceptable carrier are also provided.

The present invention also provides compositions comprising an antibody which specifically reacts with an HNF3δ protein of the invention.

The invention also provides for methods of treating conditions associated with excessive or insufficient HNF3δ activity, including the ability to regulate the transcription of one or more genes which are implicated in the formation, differentiation, proliferation and/or maintenance of cells and/or tissue, such as organ tissue including liver, lungs and pancreas, by administering to a mammalian subject a therapeutically effective amount of a pharmaceutical composition comprising an HNF3δ protein (as protein or in the form of a polynucleotide, for example, through gene therapy). The protein compositions may be stabilized through association with other factors and/or alterations to the amino acid sequence. In particular, the invention provides methods of treating conditions associated with the transcription, either positively or negatively, of one or more genes which are involved in the production of insulin-producing beta cells, or other cell types typically found in the islets of Langerhans or other pancreatic cells, as well as other organ tissues such as liver, lung, cardiac, and kidney tissue, and including the formation, growth, proliferation, differentiation and/or maintenance of such cells, tissue or organs.

As used herein, the term "HNF3δ protein" refers to the human HNF3δ protein, having the amino acid sequence specified in SEQUENCE ID NO: 4, respectively, as well as homologues of this protein found in other species; and other proteins which are closely related structurally and/or functionally to HNF3δ. Examples of "HNF3δ proteins" include rat HNF3δ protein, having the amino acid sequence of SEQUENCE ID NO: 2, as well as homologues in other species, preferably human and other mammals. It is also known that HNF related proteins also exist in other species, including family members in *Drosophila, Xenopus, C. elegans* as well as in rats, mice and humans.

As used herein, the term "HNF3δ activity" refers to one or more of the activities which are exhibited by the HNF3δ proteins of the present invention. In particular, "HNF3δ activity" includes the ability to bind HNF3δ DNA recognition sites, such as the SAAB5.1 recognition site described further below. "HNF3δ activity" further includes the ability to regulate the transcription of one or more genes which are implicated in the formation, differentiation, proliferation and/or maintenance of cells and/or tissue, such as organ tissue including liver, lungs and pancreas. HNF3δ activity may also include the ability to demonstrate effects upon the growth and/or differentiation of embryonic cells and/or stem cells. Thus, the proteins or compositions of the present invention may also be useful for treating cell populations, such as embryonic cells or stem cell populations, to enhance or enrich the growth and/or differentiation of the cells. HNF3δ may be capable of inducing the formation of pancreatic tissue by regulating the expression of the pancreas-specific gene IDX1. This is based upon the inventors' findings that HNF3δ could activate transcription of a reporter gene in cultured cells by binding to upstream HNF3δ recognition sequences [multiple copies of 5'-agattgagta-3' (SAAB5. 1), HNF3δ recognition sequences selected in vitro], and that similar HNF3δ recognition sequences were identified within the promoter sequence of IDX1. In particular then, "HNF3δ activity" may include the ability to regulate the transcription, either positively or negatively, of one or more genes which are involved in the production of insulin-producing beta cells, or other cell types typically found in the islets of Langerhans or other pancreatic cells, as well as other organ tissues such as liver, lung, cardiac, and kidney tissue, and may therefore be utilized to enhance and/or inhibit the formation, growth, proliferation, differentiation and/or maintenance of such cells, tissue or organs. "HNF3δ activity" also includes the activities of HNF3δ protein in the assays described in the examples herein.

Rat and Human HNF3δ

The rat HNF3δ DNA sequence (SEQ ID NO: 1) and amino acid sequence (SEQ ID NO: 2) are set forth in the Sequence Listings. HNF3δ proteins produced from the DNA sequence demonstrate the HNF3δ activity described herein, and may be capable of inducing the formation of pancreatic tissue. HNF3δ proteins may be further characterized by the ability to demonstrate activity in the assays described below.

It is expected that other species, particularly human, have DNA sequences homologous to rat HNF3δ. The invention, therefore, includes methods for obtaining the DNA sequences encoding human HNF3δ, the DNA sequences obtained by those methods, and the human protein encoded by those DNA sequences. This method entails utilizing the rat HNF3δ nucleotide sequence or portions thereof to design probes to screen libraries for the human gene or coding sequences or fragments thereof using standard techniques. Thus, the present invention includes DNA sequences from other species, particularly, human, which are homologous to rat HNF3δ can be obtained using the rat HNF3δ sequence. A DNA sequence encoding the complete human HNF3δ protein (SEQ ID NO: 3) and the corresponding amino acid sequence (SEQ ID NO: 4) are set forth herein. As described herein, these sequences were isolated using a portion of the rat HNF3δ sequence as a probe. The human HNF3δ sequence of SEQ ID NO: 3 may also be used in order to design probes to obtain further human HNF3δ gene or coding sequences through standard techniques. The rat and human HNF3δ sequences, or portions thereof, may also be used as probes, or to design probes, in order to obtain other related DNA sequences, as well as finding homologues to the HNF3δ protein in other species. The HNF3δ proteins of the present invention, such as human HNF3δ, may be produced by culturing a cell transformed with the correlating DNA sequence, and recovering the nuclear extract. The purified expressed protein is substantially free from other proteinaceous materials with which it is co-produced, as well as from other contaminants. The recovered purified protein is contemplated to exhibit HNF3δ activity, including DNA binding activity. The purified protein of the invention may be further characterized by the ability to demonstrate activity in one or more of the assays described below.

Another aspect of the invention provides pharmaceutical compositions containing a therapeutically effective amount of a HNF3δ protein, such as rat or human HNF3δ protein, in a pharmaceutically acceptable vehicle or carrier. These compositions of the invention may be used in the formation of hormone-secreting cells of a pancreatic phenotype. These compositions may further be utilized in order to enhance and/or inhibit the formation, growth, proliferation, differentiation and/or maintenance of beta cells, and other cell types typically found in the islets of Langerhans or other pancreatic cells, as well as other organ tissues such as liver, lung, cardiac, and kidney tissue. The compositions comprising HNF3δ may be used to treat precursor or stem cells, such as pancreatic stem cells, which are able to differentiate into cells which comprise differentiated tissue or organs, such as pancreatic cells, in order to enhance the formation, differentiation, proliferation and/or maintenance of such cells, tissue or organs. Methods for forming and maintaining such cells are described, for example, in W093/00441, the disclosure of which is hereby incorporated herein by reference.

The compositions of the invention may comprise, in addition to a HNF3δ protein, other therapeutically useful agents including growth factors such as epidermal growth factor (EGF), fibroblast growth factor (FGF), transforming growth factor (TGF-α and TGF-β), activins, inhibins, bone morphogenetic proteins (BMP), and insulin-like growth factor (IGF). The compositions may also include an appropriate matrix for instance, for supporting the composition and providing a surface for pancreatic tissue growth. The matrix may provide slow release of the HNF3δ protein and/or the appropriate environment for presentation thereof.

The HNF3δ containing compositions may be employed in methods for treating a number of tissue defects, and healing and maintenance of various types of tissues and wounds. The tissues and wounds which may be treated include pancreas, but may also include epidermis, nerve, muscle, including cardiac muscle, and other tissues and wounds, and other organs such as liver, lung, cardiac, and kidney tissue. These methods, according to the invention, entail administering to a patient needing such tissue formation, wound healing or tissue repair, an effective amount of a HNF3δ protein. The HNF3δ containing compositions may also be used to treat or prevent such conditions as pancreatic cancer, and other abnormalities of organ tissue, such as pancreas, liver, lung, cardiac, and kidney tissue, and other tissues and organs. These methods may also entail the administration of a protein of the invention in conjunction with administration of at least one other protein, for example growth factors including EGF, FGF, TGF-α, TGF-β, BMP, activin, inhibin and IGF.

Still a further aspect of the invention are DNA sequences coding for expression of a HNF3δ protein. Such sequences include the sequence of nucleotides in a 5' to 3' direction illustrated in SEQ ID NO: 1 or SEQ ID NO: 3, DNA sequences which, but for the degeneracy of the genetic code, are identical to the DNA sequence SEQ ID NO: 1 or SEQ ID NO: 3, and DNA sequences which encode the protein of SEQ ID NO: 2 or SEQ ID NO: 4. Further included in the present invention are DNA sequences which hybridize under stringent conditions with the DNA sequence of SEQ ID NO: 1 or SEQ ID NO: 3 and encode a protein having the ability to enhance and/or inhibit the formation, growth, proliferation, differentiation, maintenance of pancreatic cells, such as insulin-producing beta cells, or other organ tissues such as liver, lung, cardiac, and kidney tissue. Preferred DNA sequences include those which hybridize under stringent conditions [see, T. Maniatis et al, *Molecular Cloning (A Laboratory Manual)*, Cold Spring Harbor Laboratory (1982), pages 387 to 389]. It is generally preferred that such DNA sequences encode a polypeptide which is at least about 80% homologous, and more preferably at least about 90% homologous, to the mature human HNF3δ amino acid sequence shown in SEQ ID NO: 4. Finally, allelic or other variations of the sequences of SEQ ID NO: 3, whether such nucleotide changes result in changes in the peptide sequence or not, but where the peptide sequence still has HNF3δ activity, are also included in the present invention. The present invention also includes fragments of the DNA sequence of HNF3δ shown in SEQ ID NO: 1 or SEQ ID NO: 3 which encode a polypeptide which retains the activity of HNF3δ protein. The determination whether a particular variant or fragment of the HNF3δ proteins of the present invention, such as those shown in SEQ ID NO: 2 and SEQ ID NO: 4, maintains HNF3δ activity, is routinely performed using the assays described in the examples herein.

The DNA sequences of the present invention are useful, for example, as probes for the detection of MRNA encoding HNF3δ in a given cell population. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a recombinant HNF3δ protein of the invention in which a cell line transformed with a DNA sequence encoding a HNF3δ protein in operative association with an expression control sequence therefor, is cultured in a suitable culture medium and a HNF3δ protein is recovered and purified therefrom. This process may employ a number of known cells both prokaryotic and eukaryotic as host cells for expression of the polypeptide. The vectors may also be used in gene therapy applications. In such use, the vectors may be transfected into the cells of a patient ex vivo, and the cells may be reintroduced into a patient. Alternatively, the vectors may be introduced into a patient in vivo through targeted transfection.

In a preferred embodiment of the invention, vectors are prepared using one or more non-native regulatory elements, such as promoters and/or enhancers operatively associated with the coding sequence for HNF3δ, in order to achieve expression of HNF3δ in desired cell tissue and/or at a desired time in development. For example, a vector may be constructed using the promoter element from the well-characterized IDX1 gene, which is known to be constitutively expressed in pancreatic cells, including beta cells, during development. By operatively associating the promoter from the IDX gene with the coding sequence for HNF3δ, and transforming suitable cells, such as pancreatic stem cells as described in W093/00441, one can express HNF3δ in these cells, thus promoting the desired effects of formation, growth, proliferation, differentiation and/or maintenance of pancreatic beta cells which are able to secrete insulin, either in in vitro culture or in vivo.

Still a further aspect of the invention are HNF3δ proteins or polypeptides. Such polypeptides are characterized by having an amino acid sequence including the sequence illustrated in SEQ ID NO: 2 or SEQ ID NO: 4, variants of the amino acid sequence of SEQ ID NO: 2 or SEQ ID NO: 4, including naturally occurring allelic variants, and other variants in which the protein retains the ability to enhance and/or inhibit the formation, growth, proliferation, differentiation and/or maintenance of pancreatic or other organ tissue, such as liver, lung, cardiac, and kidney tissue, characteristic of HNF3δ. Preferred polypeptides include a polypeptide which is at least about 80% homologous, and more preferably at least about 90% homologous, to the mature HNF3δ amino acid sequences shown in SEQ ID NO: 2 or SEQ ID NO: 4. Finally, allelic or other variations of the sequences of SEQ ID NO: 2 or SEQ ID NO: 4, whether such amino acid changes are induced by mutagenesis, chemical alteration, or by alteration of DNA sequence used to produce the polypeptide, where the peptide sequence still has HNF3δ activity, are also included in the present invention. The present invention also includes fragments of the amino acid sequence of HNF3δ shown in SEQ ID NO: 2 or SEQ ID NO: 4 which retain the activity of HNF3δ protein. One skilled in the art can readily produce such variations and fragments of the HNF3δ protein using techniques known in the art, and can readily assay them for activity, as described in the examples herein.

The purified proteins of the present inventions may be used to generate antibodies, either monoclonal or polyclonal, to HNF3δ and/or other related HNF3δ proteins, using methods that are known in the art of antibody production. Thus, the present invention also includes antibodies to human HNF3δ and/or other HNF3δ proteins. The antibodies may be useful for purification of HNF3δ proteins, or for inhibiting or preventing the effects of HNF3δ proteins either in vitro or in vivo. The HNF-3δ protein and related proteins may be useful for inducing the growth and/or differentiation of embryonic cells and/or stem cells. Thus, proteins or compositions of the present invention may also be useful for treating cell populations, such as embryonic cells or stem cell populations, to enhance, enrich or to inhibit the growth and/or differentiation of the cells. For example, the HNF3δ protein may be useful for treating cell populations to enhance and/or inhibit the formation, differentiation, proliferation and/or maintenance of insulin-producing beta cells, or other cells of pancreatic phenotype. The treated cell populations may be useful for, among other things, gene therapy applications, as described below.

Description of the Sequences

SEQ ID NO: 1 is a nucleotide sequence encoding the rat HNF3δ polypeptide.

SEQ ID NO: 2 is the amino acid sequence containing the rat HNF3δ polypeptide.

SEQ ID NO: 3 is a nucleotide sequence encoding the human HNF3δ.

SEQ ID NO: 4 is the amino acid sequence containing the human HNF3δ polypeptide.

DETAILED DESCRIPTION OF THE INVENTION

HNF3δ

The rat HNF3δ nucleotide sequence (SEQ ID NO: 1) and encoded amino acid sequence (SEQ ID NO: 2) are set forth in the Sequence listings herein. The coding sequence of the mature rat HNF3δ protein begins at nucleotide #88 and continues through nucleotide #2400. Purified rat HNF3δ proteins of the present invention are produced by culturing a host cell transformed with a DNA sequence comprising the DNA coding sequence of SEQ ID NO: 1 from nucleotide #88 to #2400, or from nucleotide #1 to #3441, and recovering and purifying from the cell extract a protein which contains the amino acid sequence or a substantially homologous sequence as represented by amino acids #1 to #771 of SEQ ID NO: 2.

The human HNF3δ sequence of the present invention is obtained using the whole or fragments of the rat HNF3δ DNA sequence, or a partial human HNF3δ sequence, as a probe. Thus, the human HNF3δ DNA sequence of SEQ ID NO: 3 corresponds well to the DNA sequence of the rat HNF3δ DNA sequence shown in SEQ ID NO: 1. The human HNF3δ protein comprises the sequence of amino acids #1 to #763 of SEQ ID NO: 4.

The HNF3δ proteins of the present invention, include polypeptides having a molecular weight of about 85.2 kd, pI 7.75 in monomeric form, said polypeptide comprising the amino acid sequence of SEQ ID NO: 2 or SEQ ID NO: 4 and having the ability to exhibit HNF3δ activity, or to demonstrate activity in one or more of the assays described in the examples herein. The HNF3δ proteins recovered from the culture medium are purified by isolating them from other proteinaceous materials from which they are co-produced and from other contaminants present. HNF3δ proteins may be characterized by the ability to exhibit HNF3δ activity, including the ability to bind HNF3δ DNA recognition sequences, or to demonstrate activity in one or more of the assays described in the examples herein.

The HNF3δ proteins provided herein also include factors encoded by the sequences similar to those of SEQ ID NO: 1 or SEQ ID NO: 3, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO: 2 or SEQ ID NO: 4. These sequences, by virtue of sharing primary, secondary, or tertiary structural and conformational characteristics with HNF3δ polypeptides of SEQ ID NO: 2 or SEQ ID NO: 4 may possess biological properties in common therewith. Thus, these modifications and deletions of the native HNF3δ may be employed as biologically active substitutes for naturally-occurring HNF3δ polypeptides in therapeutic processes. It can be readily determined whether a given variant of HNF3δ maintains the biological activity of HNF3δ by subjecting both HNF3δ and the variant of HNF3δ to the assays described in the examples.

Other specific mutations of the sequences of HNF3δ proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Such variants of HNF3δ are within the present invention. Additionally, bacterial expression of HNF3δ protein will result in production of a non-glycosylated protein, even if the glycosylation sites are left unmodified. Such bacterially produced versions of HNF3δ are within the present invention.

The present invention also encompasses the novel DNA sequences, free of association with DNA sequences encoding other proteinaceous materials, and coding for expression of HNF3δ proteins. These DNA sequences include those depicted in SEQ ID NO: 1 and SEQ ID NO: 3 in a 5' to 3' direction and those sequences which hybridize thereto under stringent hybridization conditions [for example, 0.1X SSC, 0.1% SDS at 65° C.; see, T. Maniatis et al, *Molecular Cloning (A Laboratory Manual)*, Cold Spring Harbor Laboratory (1982), pages 387 to 389] and encode a protein having HNF3δ activity. These DNA sequences also include those which comprise the DNA sequence of SEQ ID NO: 1 or SEQ ID NO: 3 and those which hybridize thereto under stringent hybridization conditions and encode a protein having HNF3δ activity.

Similarly, DNA sequences which code for HNF3δ proteins coded for by the sequences of SEQ ID NO: 1 or SEQ ID NO: 3, or HNF3δ proteins which comprise the amino acid sequence of SEQ ID NO: 2 or SEQ ID NO: 4, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 or SEQ ID NO: 3 which are caused by point mutations or by induced modifications (including insertion, deletion, and substitution) to enhance the activity, half-life or production of the polypeptides encoded are also encompassed in the invention.

Another aspect of the present invention provides a novel method for producing HNF3δ proteins. The method of the present invention involves culturing a suitable cell line, which has been transformed with a DNA sequence encoding a HNF3δ protein of the invention, under the control of known regulatory sequences. The transformed host cells are cultured and the HNF3δ proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293: 620–625 (1981), or alternatively, Kaufman et al, *Mol. Cell. Biol.*, 5(7): 1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis, Pseudomonas,* other bacilli and the like may also be employed in this method. For expression of the protein in bacterial cells, DNA encoding the propeptide of HNF3δ is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8: 277–298 (Plenum Press 1986) and references cited therein.

Another aspect of the present invention provides vectors for use in the method of expression of these novel HNF3δ polypeptides. Preferably the vectors contain the full novel DNA sequences described above which encode the novel factors of the invention. Additionally, the vectors contain appropriate expression control sequences permitting expression of the HNF3δ protein sequences. Alternatively, vectors incorporating modified sequences as described above are also embodiments of the present invention.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

In order to produce rat, human or other mammalian HNF3δ proteins, the DNA encoding it is transferred into an appropriate expression vector and introduced into mammalian cells or other preferred eukaryotic or prokaryotic hosts by conventional genetic engineering techniques. The preferred expression system for biologically active recombinant human HNF3δ is contemplated to be stably transformed mammalian cells.

One skilled in the art can construct mammalian expression vectors by employing the sequence of SEQ ID NO: 1 or SEQ ID NO: 3, or other DNA sequences encoding HNF3δ proteins or other modified sequences and known vectors, such as pED6. The mammalian expression vector pED6 is a derivative of pED, which is described in Kaufman et al., *Nucleic Acids Research*, 19: 4485–4490 (1991).

The construction of vectors may involve modification of the HNF3δ DNA sequences. For instance, HNF3δ cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of HNF3δ proteins.

One skilled in the art can manipulate the sequences of SEQ ID NO: 1 or SEQ ID NO: 3 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified HNF3δ coding sequence could then be inserted into a known bacterial vector using procedures such as described in T. Taniguchi et al., *Proc. Natl Acad. Sci. USA*, 77: 5230–5233 (1980). This exemplary bacterial vector could then be transformed into bacterial host cells and a HNF3δ protein expressed thereby.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a HNF3δ protein of the invention in mammalian cells may involve the construction of cells containing multiple copies of the heterologous HNF3δ gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159: 601–629 (1982). This approach can be employed with a number of different cell types.

For example, a plasmid containing a DNA sequence for a HNF3δ protein of the invention in operative association with other plasmid sequences enabling expression thereof and the DHFR expression plasmid pED6 can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5uM MTX) as described in Kaufman et al., *Mol Cell Biol.*, 5: 1750 (1983). Transformants are cloned, and biologically active HNF3δ expression is monitored by assay in one of the assays described in the examples below, such as the DNA binding assay. HNF3δ protein expression should increase with increasing levels of MTX resistance. HNF3δ polypeptides are characterized using standard techniques known in the art such as pulse labeling with [35S] methionine or cysteine and polyacrylamide gel electrophoresis. Similar procedures can be followed to produce other related HNF3δ proteins.

A protein of the present invention, which demonstrates HNF3δ activity, has application in the induction, formation, growth, differentiation, proliferation and/or maintenance and healing of tissue such as pancreatic tissue, and other organ tissue, in humans and other animals. Such a preparation employing. a HNF3δ protein may have prophylactic use in preventing pancreatic tumors, diabetes and other pancreatic tissue disorders. De novo formation of beta cells, islet of Langerhans cells, and other cells of pancreatic phenotype, induced by a HNF3δ protein contributes to the repair of congenital, trauma induced, or oncologic tissue defects or conditions. A HNF3δ protein may be used in the treatment of pancreatic disease, and in other tissue and organ repair processes. Such agents may provide an environment to attract suitable stem cells, stimulate growth and proliferation of pancreas-forming cells or induce differentiation of progenitors of pancreas-forming cells, and may also support the regeneration of other tissues and organs. HNF3δ polypeptides of the invention may also be useful in the treatment of organ disorders such as pancreitis or diabetes.

The proteins of the invention may also be used in wound healing and in related tissue repair. The types of wounds include, but are not limited to burns, incisions and ulcers. (See, e.g. PCT Publication W084/01106 for discussion of wound healing and related tissue repair). It is further contemplated that proteins of the invention may increase neuronal, astrocytic and/or glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, lung, cardiac, and kidney tissue. The proteins of the present invention may also have value as a dietary supplement or as a component of cell culture media. For this use, the proteins may be used in intact form, or may be predigested to provide a more readily absorbed supplement.

The proteins of the invention may also have other useful properties characteristic of the HNF3δ family of proteins. Such properties include angiogenic, chemotactic and/or chemoattractant properties, and effects on cells including differentiation responses, cell proliferative responses and responses involving cell adhesion, migration and extracellular matrices. These properties make the proteins of the invention potential agents for wound healing, reduction of fibrosis and reduction of scar tissue formation. The proteins of the invention may also be useful for the induction of formation of cells capable of secreting valuable hormones, such as insulin, glucagon, or other endocrine or exocrine hormones.

A further aspect of the invention is a therapeutic method and composition for treating disorders of the pancreas, diabetes, and other conditions related to pancreatic tissue disorders or diseases. The invention further comprises therapeutic methods and compositions for wound healing and tissue repair. Such compositions comprise a therapeutically effective amount of at least one HNF3δ protein of the present invention in admixture with a pharmaceutically acceptable vehicle, carrier or matrix. It is further contemplated that compositions of the invention may increase neuronal survival and therefore be useful in transplantation and treatment of conditions exhibiting a decrease in neuronal survival.

It is expected that the proteins of the invention may act in concert with or perhaps synergistically with other related proteins and growth factors. Further therapeutic methods and compositions of the invention therefore comprise a therapeutic amount of at least one HNF3δ protein of the invention with a therapeutic amount of at least one other protein, such as a member of the TGF-β superfamily of proteins, which includes the BMPs, GDFs and other proteins. The composition may include other agents and growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), leukemia inhibitory factor (LIF/HILDA/DIA), insulin-like growth factors (IGF-I and IGF-II). Portions of these agents may also be used in compositions of the present invention.

The preparation and formulation of such physiologically acceptable protein compositions, having due regard to pH, isotonicity, stability and the like, is within the skill of the art. The therapeutic compositions are also presently valuable for veterinary applications due to the lack of species specificity in HNF proteins. Particularly domestic animals and thoroughbred horses in addition to humans are desired patients for such treatment with the HNF3δ proteins of the present invention.

The therapeutic method includes administering the composition topically, systemically, or locally as by injection or implantation. When administered, the therapeutic composition for use in this invention is, of course, in a pyrogen-free, physiologically acceptable form. Further, the composition may desirably be encapsulated or injected in a viscous form for delivery to the site of pancreatic or other tissue damage. Topical administration may be suitable for wound healing and tissue repair. Therapeutically useful agents other than the HNF3δ proteins which may also optionally be included in the composition as described above, may alternatively or additionally, be administered simultaneously or sequentially with the HNF3δ composition in the methods of the invention.

For implantation, the composition preferably includes a matrix capable of delivering HNF3δ proteins to the site of pancreatic or other tissue damage, providing a structure for the developing tissue and optimally capable of being resorbed into the body. The matrix may provide slow release of HNF3δ and/or other protein, as well as proper presentation and appropriate environment for cellular infiltration. Such matrices may be formed of materials presently in use for other implanted medical applications. The choice of matrix material is based on biocompatibility, biodegradability, mechanical properties, cosmetic appearance and interface properties. The particular application of the HNF3δ compositions will define the appropriate formulation.

The dosage regimen will be determined by the attending physician considering various factors which modify the action of the HNF3δ protein, e.g. amount of tissue desired to be formed, the site of tissue damage, the condition of the damaged tissue, the size of a wound, type of damaged tissue, the patient's age, sex, and diet, the severity of any infection, time of administration and other clinical factors. The dosage may vary with the type of matrix used in the reconstitution and the types of HNF3δ proteins in the composition. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor I), to the final composition, may also affect the dosage.

Progress can be monitored by periodic assessment of tissue growth and/or repair. The progress can be monitored, for example, x-rays, histomorphometric determinations and tetracycline labeling.

The following examples illustrate practice of the present invention in recovering and characterizing rat HNF3δ protein and employing the DNA to recover human HNF3δ and other HNF3δ, obtaining the human proteins and expressing the proteins via recombinant techniques.

EXAMPLES

EXAMPLE 1

Isolation of DNA Encoding HNF3δ

DNA encoding HNF3δ was isolated by degenerate RT-PCR using INS-1 polyA+ RNA as templates and two sets of degenerate oligonucleotides, HFH-1 (5'-aarcchcchtawtcntayat-3') and HFH-2 (5'-rtgyckratngarttctgcca-3'), designed against two conserved blocks of homology within the first half of the HFH DNA binding domain. Based on the sequence information of this 153 bp HNF3δ PCR product, a 30-mer oligonucleotide was synthesized to screen an INS-1 cDNA library resulting in the isolation of a 3.0-kb cDNA. This 3.0-kb cDNA misses the translational start codon; therefore the 5' end of the HNF3δ transcript was synthesized by the PCR-based procedure, 5'-RACE. The PCR-generated 5' cDNA was assembled with the 3.0-kb cDNA at the EcoRV site to give a near full length cDNA of ~3.4-kb.

Conceptual translation of the 3.4-kb cDNA sequence revealed a 771-amino acid ORF that can encode an 85.2-kD polypeptide. Coupled in vitro transcription-translation of the 3.4-kb cDNA led to the synthesis of a 95-kD polypeptide. Phosphorylation of the carboxyl terminal portion of the HNF3δ protein might explain its decreased mobility on SDS-PAGE gels.

To isolate cDNAs encoding human HNF3δ, we screened an human pancrease adenocarcinoma library and a testis library using a 605-bp rat HNF3δ SacI-SacI fragment (nucleotide #556 to #1162), which spans the DNA binding domain, as probe. Using this procedure, four partial human cDNAs have been isolated. The full length cDNA, including the 5' end of the human HNF3δ cDNA can be cloned using 5'-RACE.

EXAMPLE 2

Expression Analysis of HNF3δ by Northern Blots

HNF3δ was cloned from INS-1 cells. To determine whether HNF3δ expression is limited to pancreatic β cells, we studied by Northern analysis the expression of the gene in a variety of insulin-secreting (rat INS-1 and RIN1046–38; mouse bTC1 and bTC6), glucagon-secreting (rat RIN56A, mouse aTC1) and somatotstatin-secreting (rat RIN1027-B2) cells. Using the 3.4 kb HNF3δ cDNA as a probe, we detected a strong ~3.4 kb doublet and a weaker ~4.0 kb transcript in total RNAs prepared from INS-1 cells. The 3.4 kb HNF3δ cDNA corresponds well in size with the strong doublet although more cDNA analysis is required to confirm the identity of the multiple transcripts. Expression of these transcripts were detectable in all the insulinoma cell lines tested. HNF3δ expression was also detectable at a lower level in the neuronal cell line, PC12, but was undetectable in the hepatic cell line, HepG2 cells.

To understand how HNF3δ expression correlates with pancreas organogenesis, we analyzed by Northern blots total RNAs isolated from embryonic, neonate and adult pancreas. HNF3δ was highly expressed when the pancreatic bud first forms at the embryonic 12 day (e12) and remained high in e14 and e18 pancreata. Interestingly, expression did not persist through adulthood. HNF3δ expression was decreased in neonate pancreas and was undetectable in adult pancreas. Analysis of islet total RNA also did not show detectable expression of HNF3δ. This suggests that the lack of adult pancreas expression of HNF3δ is not due to the restriction of expression to endocrine cells, which represent less than 5% of the pancreas. Liver samples similarly analyzed indicated that the HNF3δ gene was expressed in e14 but not in adult liver. It is interesting to note that dramatic pancreas organogenesis occurs during the period from e12 to neonate, which corresponds to the period of high level of HNF3δ expression in pancreas.

To study whether HNF3δ is expressed in other adult tissues, total RNAs from different rat tissues were analyzed by Northern blots. HNF3δ expression was detectable in adult duodenum, thymus and fat, and in large intestine at a lower level. Additionally, we probed a human endocrine system multiple tissue Northern blot using the rat HNF3δ cDNA. A 4.0 kb transcript was detectable in both thymus and testis, but not in pancreas and other endocrine tissues. This finding is consistent with the rat tissue Northern data.

In summary, HNF3δ is highly expressed in insulinoma cell lines, embryonic pancreas and liver, and adult gut, thymus, fat and testis. The thymus expression can explain the cloning of human Mpp2/HNF3δ from the lymphoblastic cell line MOLT-4

ATCC Deposits

A plasmid containing rat HNF3δ DNA sequence was deposited with the American Type Culture Collection (ATCC), 12301 Parklawn Drive, Rockville, Md. on Sep. 3, 1996 and was accorded the accession number ATCC 97704. A plasmid containing partial human HNF3δ DNA sequence was deposited with the American Type Culture Collection (ATCC), 10801 University Boulevard, Manassas, Va. 20110-2209 on Sep. 3, 1996 and was accorded the accession number ATCC 97705. Using these plasmids, one can readily prepare expression vectors and other materials useful for the practice of the present invention.

EXAMPLE 3

Biological Activity of Expressed HNF3 δ

To test whether HNF3δ can function as a transcriptional activator, we co-transfected cultured cells with the HNF3δ cDNA and a reporter plasmid carrying 5 copies of the HNF3δ SAAB5. 1 binding sites. We have used both NIH3T3 and HeLa cells for transfection. Northern analysis of total RNAs prepared from both cells indicated that HNF3δ was expressed in NHI3T3 cells but not in HeLa cells. The HNF3δ binding sites were placed upstream of a TATA box secreted alkaline phosphatase (SEAP) coding sequence. With an expression plasmid/reporter plasmid ratio of 5:1, we were able to detect more than ten fold increase in transcriptional activation of the SEAP reporter gene. Since similar HNF3δ recognition sequences could be identified within the promoter sequence of IDX1, HNF3δ may also activate transcription by binding to the HNF3δ SAAB5.1 recognition sequences within the IDX1 promoter.

EXAMPLE4

Construction of IDX-1-HNF3δ Vector for Overexpression of HNF3δ and the Analysis of IDX-1-HNF3δ Mice Northern blot analysis indicates that HNF3δ is highly expressed in developing pancreas from the very beginning of overt pancreas morphogenesis at e12. The interesting question to ask is whether overexpression of the HNF3δ gene product at this early stage of pancreas development will lead to altered fate determination. To achieve this pancreas-specific overexpression, we can subclone the HNF3δ cDNA into pIT2 which contains an upstream pancreas-specific IDX-1 promoter. Pioneer experiments by Dr. C. Miller (Genetics Institute, Inc, personal communication) have demonstrated that the IDX- 1 promoter within pIT2 can direct high level mis-expression of candidate genes. The IDX-1-HNF3δ construct can be injected into fertilized oocytes to generate Fo transgenic mice and the animals recovered at around 20 dpc for analyzing pancreas and gut development by histochemistry and immunostaining.

The fact that HNF3δ is also highly expressed in thymus, testis, fat (from pregnant females) and gut areas where there are high content of progenitor cells with high proliferative activity and human HNF3δ and MPP2 are related genes suggests that HNF3δ might play a role in regulating the development of progenitor cells. The prediction is that overexpression of HNF3δ at early pancreas development might increase the number and/or proliferative potential of early pancreatic progenitor cells leading to general hypertrophy or enhanced development of specific lineage e.g., endocrine versus exocrine IDX-1 expression becomes restricted to the β-cell lineage later in pancreas development. Visual examination of the gut of 20 dpc transgenic animals followed by further innumohistochemical analysis should reveal any developmental defect due to overexpression of HNF3δ. Immunostaining with anti-glucagon and anti-insulin antisera should indicate whether the development of the endocrine lineages are altered.

EXAMPLE 5

Production and Analysis of Knockout Mouse for HNF3δ

To understand the functional role of HNF3δ during mouse development, a loss-of-function mutation can be generated by ES cell-based homologous recombination. A targeting construct can be made with the neomycin-resistant gene as selectable marker and >5 kb (>1 kb at either end) of flanking HNF3δ genomic sequences to allow for efficient homologous recombination. One copy of the thymidine kinase gene will also be introduced at one end to allow for negative selection against non-homologous recombination by culturing in the presence of gancyclovir. The bacterial β-galactosidase gene can also be cloned in-frame and downstream of the 5' HNF3δ genomic sequence such that the majority of the HNF3δ coding sequences including the DNA binding domain will be replaced by the β-galactosidase gene following homologous recombination. The β-galactosidase reporter gene would allow the developmental expression of HNF3δ to be analyzed by X-gal staining in heterozygous animals.

The linearized targeting construct will be eletrophorated into ES cells followed by selection in G418 and gancyclovir-containing medium. Neo$^r$tk-colonies will be isolated and genomic DNA prepared for PCR and Southern blot analysis for identifying clones carrying the right homologous recombination events. Positive ES lines will be injected into 3.5 dpc mouse blastocytes for generating $F_0$ chimeric animals. If the ES cells can contribute to the germ line, backcrossing of the chimeric animals will give agouti $F_1$ pups which will be genotyped by tail DNA analysis to identify the heterozygous animals. Further mating of the heterozygous animals will generate both heterozygous pups for analysis of expression by X-gal staining and homozygous pups for phenotypic analysis, assuming that the knockout animals are not early lethal. If a pancreatic phenotype is observed, we can also try to rescue the phenotype by crossing the knockout animals to IDX-1-HNF3δ mice.

EXAMPLE 6

Embryonic Stem Cell Assay

In order to assay the effects of the HNF3δ proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for immunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with conditioned defined media (CDM) containing much lower amounts of FBS.

At the end of the treatment period (ranging from 7–21 days) RNA is harvested from the cells and analyzed by quantitative multiplex PCR for the following markers: Brachyury, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 3441 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 88..2400

( x i ) SEQUENCE DESCRIPTION: SEQ ID NO:1:

```
GCCTGGCTCG GCCCCGCGTG GAGCAGCGGT GGCCTGTGAG GGTCAAAGCT TGTGATTCTC          60

GATGGAGAGT GAAAGCACAG CTTCATG ATG AGA ACC AGC CCC CGG CGG CCA             111
                              Met Arg Thr Ser Pro Arg Arg Pro
                                1               5

CTG ATT CTC AAG AGA CGG AGG CTG CCC CTT CCT ATT CAA AAT GCC CCG           159
Leu Ile Leu Lys Arg Arg Arg Leu Pro Leu Pro Ile Gln Asn Ala Pro
         10              15                  20

AGT GAA ACC TCA GAG GAA GAA GCA AAG AGA TCC CCT GGA CAG CAG GAG           207
Ser Glu Thr Ser Glu Glu Glu Ala Lys Arg Ser Pro Gly Gln Gln Glu
 25                  30              35                      40

CCT ACT CAA GCA CAG GCC TCC CAA GAT GTG GCA GAG TCC AGC TCT TGC           255
Pro Thr Gln Ala Gln Ala Ser Gln Asp Val Ala Glu Ser Ser Ser Cys
                 45                  50                  55

AAA TTT CCA GCT GGA ATC AAG ATT ATC AAC CAC CCA ACC GTG CCC AAC           303
Lys Phe Pro Ala Gly Ile Lys Ile Ile Asn His Pro Thr Val Pro Asn
             60                  65                  70

ACA CAA GTG GTG GCT ATC CCC AAC AAC GCG GAC ATC CAG AGC ATC ATC           351
Thr Gln Val Val Ala Ile Pro Asn Asn Ala Asp Ile Gln Ser Ile Ile
         75                  80                  85

ACA GCG CTG ACT GCC AAA GGG AAA GAG AGT GGC AGC AGT GGG CCC AAC           399
Thr Ala Leu Thr Ala Lys Gly Lys Glu Ser Gly Ser Ser Gly Pro Asn
 90                  95                 100

AAG TTC ATC CTC ATC AGC TCT GGA GGG GCC TCA TCT CAT CCT CCT GAT           447
Lys Phe Ile Leu Ile Ser Ser Gly Gly Ala Ser Ser His Pro Pro Asp
105                 110                 115                 120

CCT CAA TCT CAA GCC CAA ACC AGC ACT GAT TCC AAG AGA ACA GAA CTG           495
Pro Gln Ser Gln Ala Gln Thr Ser Thr Asp Ser Lys Arg Thr Glu Leu
                125                 130                 135

ATC ACC GAG ACG TTG GGA CCA AAG CCA GGG GCT AAG GGT GTG CCT GTT           543
Ile Thr Glu Thr Leu Gly Pro Lys Pro Gly Ala Lys Gly Val Pro Val
            140                 145                 150

CCC AAG CCA CCT GGA GCT CTT CCA AGG CAA AGA CAG GAG AGC TGT GGT           591
Pro Lys Pro Pro Gly Ala Leu Pro Arg Gln Arg Gln Glu Ser Cys Gly
            155                 160                 165

GGT GAA GCG GCC GGC TGC ACA CTG GAC AAC AGC TTA ACC AAT ATC CAG           639
Gly Glu Ala Ala Gly Cys Thr Leu Asp Asn Ser Leu Thr Asn Ile Gln
170                 175                 180

TGG CTT GGA AAG ATG AGT TCT GAT GGG CTG GGC CGC TGC AGC ATT AAG           687
Trp Leu Gly Lys Met Ser Ser Asp Gly Leu Gly Arg Cys Ser Ile Lys
185                 190                 195                 200

CAG GAA CTG GAA GAG AAG GAG AAT TGT CAC CTG GAG CAG AAT CGG GTT           735
Gln Glu Leu Glu Glu Lys Glu Asn Cys His Leu Glu Gln Asn Arg Val
```

```
AAG GTT GAG GCG CCC TCA AGA GCA TCA GTG TCT TGG CAG GAC TCT GTG       783
Lys Val Glu Ala Pro Ser Arg Ala Ser Val Ser Trp Gln Asp Ser Val
            220                 225                 230

TCT GAG AGG CCA CCC TAC TCC TAT ATG GCC ATG ATA CAG TTC GCG ATC       831
Ser Glu Arg Pro Pro Tyr Ser Tyr Met Ala Met Ile Gln Phe Ala Ile
        235                 240                 245

AAC AGC ACT GAG AGG AAG CGT ATG ACC TTG AAG GAT ATC TAC ACT TGG       879
Asn Ser Thr Glu Arg Lys Arg Met Thr Leu Lys Asp Ile Tyr Thr Trp
    250                 255                 260

ATC GAG GAC CAC TTC CCT TAT TTT AAG CAC ATT GCC AAG CCA GGC TGG       927
Ile Glu Asp His Phe Pro Tyr Phe Lys His Ile Ala Lys Pro Gly Trp
265                 270                 275                 280

AAG TGT TGG CAC CAG GCC TAC CAC AAG CTC GGG CCA CAG AAC TCT ATT       975
Lys Cys Trp His Gln Ala Tyr His Lys Leu Gly Pro Gln Asn Ser Ile
                285                 290                 295

CGT CAC AAC CTT TCT CTC CAT GAC ATG TTT GTT CGA GAA ACA TCT GCC      1023
Arg His Asn Leu Ser Leu His Asp Met Phe Val Arg Glu Thr Ser Ala
            300                 305                 310

AAT GGC AAG GTC TCC TTC TGG ACC ATT CAC CCA AGT GCT AAT CGC TAC      1071
Asn Gly Lys Val Ser Phe Trp Thr Ile His Pro Ser Ala Asn Arg Tyr
        315                 320                 325

TTG ACA TTG GAC CAA GTG TTT AAG CCA CTG GAA CCA GGG TCT CCA CAA      1119
Leu Thr Leu Asp Gln Val Phe Lys Pro Leu Glu Pro Gly Ser Pro Gln
    330                 335                 340

TCG CCC GAG CAC TTG GAA TCA CAG CAG AAA CGA CCC AAT CCT GAG CTC      1167
Ser Pro Glu His Leu Glu Ser Gln Gln Lys Arg Pro Asn Pro Glu Leu
345                 350                 355                 360

CGT AGA AAT GTG ACC ATC AAA ACT GAA CTC CCA CTA GGC GCA CGG CGA      1215
Arg Arg Asn Val Thr Ile Lys Thr Glu Leu Pro Leu Gly Ala Arg Arg
                365                 370                 375

AAG ATG AAG CCA CTG CTC CCA CGG GTT AGC TCA TAC CTG GTG CCC ATC      1263
Lys Met Lys Pro Leu Leu Pro Arg Val Ser Ser Tyr Leu Val Pro Ile
            380                 385                 390

CAG TTC CCG GTG AAC CAG TCC CTG GTG TTA CAG CCC TCG GTG AAG GTT      1311
Gln Phe Pro Val Asn Gln Ser Leu Val Leu Gln Pro Ser Val Lys Val
        395                 400                 405

CCC TTG CCT CTG GCA GCA TCT CTT ATG AGC TCA GAG CTT GCC CGT CAT      1359
Pro Leu Pro Leu Ala Ala Ser Leu Met Ser Ser Glu Leu Ala Arg His
    410                 415                 420

AGC AAG CGA GTC CGC ATT GCA CCC AAG GTG CTG CTA TCC AAC GAA GGG      1407
Ser Lys Arg Val Arg Ile Ala Pro Lys Val Leu Leu Ser Asn Glu Gly
425                 430                 435                 440

ATA GCC CCA CTT CCT GCC ACA GAA CCC ATG AAG GAG GAG AAA CCC CTG      1455
Ile Ala Pro Leu Pro Ala Thr Glu Pro Met Lys Glu Glu Lys Pro Leu
                445                 450                 455

CTT GGA GAA GGG CTA TTG CCT TTG CTT CCT ATT CAG TCC ATT AAG GAA      1503
Leu Gly Glu Gly Leu Leu Pro Leu Leu Pro Ile Gln Ser Ile Lys Glu
            460                 465                 470

GAA GTA ATT CAG CCT GGG GAG GAC ATA CCA CAC TTA GAG AGG CCT ATC      1551
Glu Val Ile Gln Pro Gly Glu Asp Ile Pro His Leu Glu Arg Pro Ile
        475                 480                 485

AAA GTG GAG AGC CCT CCC TTG GAA GAG TGG CCC TCT CCG TGT GCA TCA      1599
Lys Val Glu Ser Pro Pro Leu Glu Glu Trp Pro Ser Pro Cys Ala Ser
    490                 495                 500

GTG AAA GAG GAA CTG TCC AAC TCC TGG GAA GAT TCT TCC TGC TCT CCT      1647
Val Lys Glu Glu Leu Ser Asn Ser Trp Glu Asp Ser Ser Cys Ser Pro
505                 510                 515                 520

ACC CCA AAG CCC AAG AAG TCC TAT TGT GGG CTT AAG TCC CCA ACA CGG      1695
Thr Pro Lys Pro Lys Lys Ser Tyr Cys Gly Leu Lys Ser Pro Thr Arg
```

-continued

```
                              525                              530                              535
TGT  GTC  TCA  GAA  ATG  CTG  GTG  ACA  AAG  CGG  AGA  GAG  AAG  AGA  GAG  GTG       1743
Cys  Val  Ser  Glu  Met  Leu  Val  Thr  Lys  Arg  Arg  Glu  Lys  Arg  Glu  Val
               540                 545                      550

AGC  CGA  TCT  CGG  AGG  AAG  CAG  CAC  CTT  CAG  CCA  CCC  TGT  CTA  GAT  GAG       1791
Ser  Arg  Ser  Arg  Arg  Lys  Gln  His  Leu  Gln  Pro  Pro  Cys  Leu  Asp  Glu
               555                 560                      565

CCT  GAA  CTC  TTC  TTC  TCA  GAG  GAC  TCC  AGC  ACA  TTT  CGG  CCA  GCC  ATG       1839
Pro  Glu  Leu  Phe  Phe  Ser  Glu  Asp  Ser  Ser  Thr  Phe  Arg  Pro  Ala  Met
     570                      575                 580

GAG  ATC  CTG  GCA  GAG  TCT  TCA  GAG  CCT  GCA  CCA  CAG  CTC  AGC  TGC  CCT       1887
Glu  Ile  Leu  Ala  Glu  Ser  Ser  Glu  Pro  Ala  Pro  Gln  Leu  Ser  Cys  Pro
585                      590                 595                           600

CAG  GAG  GAG  GGA  GGG  CCC  TTC  AAG  ACC  CCC  ATC  AAG  GAG  ACA  TTG  CCT       1935
Gln  Glu  Glu  Gly  Gly  Pro  Phe  Lys  Thr  Pro  Ile  Lys  Glu  Thr  Leu  Pro
                    605                 610                      615

GTC  TCC  TCC  ACT  CCT  AGC  AAG  TCT  GTG  CTC  TCT  AGA  GAC  CCT  GAG  TCC       1983
Val  Ser  Ser  Thr  Pro  Ser  Lys  Ser  Val  Leu  Ser  Arg  Asp  Pro  Glu  Ser
               620                 625                      630

TGG  AGG  CTC  ACA  CCC  CCA  GCC  AAA  GTT  GGG  GGG  TTA  GAT  TTC  AGC  CCA       2031
Trp  Arg  Leu  Thr  Pro  Pro  Ala  Lys  Val  Gly  Gly  Leu  Asp  Phe  Ser  Pro
          635                      640                      645

GTA  CGA  ACC  CCC  CAG  GGT  GCC  TTT  GGC  CCT  CTG  CCT  GAC  TCG  CTG  GGG       2079
Val  Arg  Thr  Pro  Gln  Gly  Ala  Phe  Gly  Pro  Leu  Pro  Asp  Ser  Leu  Gly
     650                      655                 660

CTT  ATG  GAG  CTG  AAT  ACC  ACA  CCT  CTG  AAA  AGT  GTT  CCC  CTC  TTC  GAC       2127
Leu  Met  Glu  Leu  Asn  Thr  Thr  Pro  Leu  Lys  Ser  Val  Pro  Leu  Phe  Asp
665                      670                 675                           680

TCA  CCC  CGG  GAG  CTC  CTT  AAC  TCA  GAA  GCC  TTT  GAC  CTT  GCC  TCT  GAT       2175
Ser  Pro  Arg  Glu  Leu  Leu  Asn  Ser  Glu  Ala  Phe  Asp  Leu  Ala  Ser  Asp
                    685                 690                      695

CCC  TTT  AGC  AGT  TCT  CCA  CCA  CCA  CAT  TTG  GAA  GCC  AAG  CCA  GGC  TCC       2223
Pro  Phe  Ser  Ser  Ser  Pro  Pro  Pro  His  Leu  Glu  Ala  Lys  Pro  Gly  Ser
               700                 705                      710

CCC  GAG  CTG  CAG  GTC  CCC  AGC  CTT  TCA  GCC  AAC  CGT  TCT  CTC  ACA  GAA       2271
Pro  Glu  Leu  Gln  Val  Pro  Ser  Leu  Ser  Ala  Asn  Arg  Ser  Leu  Thr  Glu
          715                      720                 725

GGC  CTT  GTC  CTG  GAC  ACA  ATG  AAT  GAT  AGC  CTC  AGC  AAG  ATC  CTT  CTA       2319
Gly  Leu  Val  Leu  Asp  Thr  Met  Asn  Asp  Ser  Leu  Ser  Lys  Ile  Leu  Leu
     730                      735                 740

GAC  ATC  AGT  TTC  CCT  GGC  CTG  GAG  GAG  GAC  CCT  CTG  GGC  CCT  GAC  AAC       2367
Asp  Ile  Ser  Phe  Pro  Gly  Leu  Glu  Glu  Asp  Pro  Leu  Gly  Pro  Asp  Asn
745                      750                 755                           760

ATC  AAC  TGG  TCT  CAG  TTC  ATC  CCT  GAG  CTG  CGA  TAGAGGCAGG  GTCTTACCCT         2420
Ile  Asn  Trp  Ser  Gln  Phe  Ile  Pro  Glu  Leu  Arg
                    765                 770

TGCCACTCAA  GCCACCAGTT  ATCCTGGCAC  TTGTGTGGCT  GGATAGTGCA  AGGCTCAGTG              2480

TACCCCAAAC  CGTCTGAGGG  AGCTAGCAGG  CAAGGGCTGA  GCGGTGCCCT  TTGACCTAAT              2540

TATGCCAAGG  TAAAAGCCAC  GTCTAAGCCA  CTGCTGGGAC  CTATGCAAGC  AATAGGATCT              2600

CCCAGAGTCC  TCCACTCCCT  GCTGGCAAGT  GAAGTGGGTG  TGACAGAGCC  GTGAGGACCA              2660

GGAAATGCCC  ACCCATTAGT  CACCTGCTGC  TCCTGGCAGG  ATAACCCTTG  TAAATGGTGT              2720

CAGTTCCCCA  AGTTGTCCTG  TAATTATAAA  TGTAGCCATA  TTCCCTTAGC  TCTCATTATC              2780

CAGAGACTGC  CAGGATGGGT  AGGGTGACAA  GGGGTTGCAT  TAGCTTCTGC  TTGTGGCCTT              2840

TGGGGGCAGG  ACCTGCAGTT  CAGCCTCTTC  ACACTGTGGG  TTCTGCTGTA  GGCTTCTAGA              2900

CACACAGGTG  TCCTTGCCAG  GACCCCACTT  ACTGCCCTTT  CCTCACAGCT  CCCCCTGGTT              2960
```

```
CTAAGCCAGT GGTACTGCAT GAAGAAATCC TGCGGCAAAG CCTATTGTCT CTGGGTGTGT    3020

GGGGACGGGT GTGCCTGAAG CAAAAGCATG GGTACTCACG TGAGTCCTTT AGGTGTTTCT    3080

CTGATCGTGT TCCCAATCAT GCCAGGGAGT CTAGCATTGA GAACTCAGGC TGAGGCCTGA    3140

GGAGGAGGAG GAAGTGACCA CTGACTTGCC TGGCTTCCTT AGCTTGCACC TGAGTTTTGC    3200

AAAAAGCCAC CCTAGACCCC ACTCTACAAG CTAGCACAAG AACACTACTG TAACTACCTA    3260

CTGAATAAAG CCCAGGTGGC CTGATCTCGG AATTGAGTGA GGGGTGATGG AGCCCGGAGA    3320

TGATGGGCAG GCCTGCACCT GCTGCATGGG CCTTGCACAG GTTGTCTCTC CACATCCTTC    3380

TTTGACTCTG AAAAAAAAAA AAAAAAAAA AAAAAAAAA AAAAAAAAA AAAAACTCGA       3440

G                                                                    3441
```

( 2 ) INFORMATION FOR SEQ ID NO:2:

( i ) SEQUENCE CHARACTERISTICS:
        ( A ) LENGTH: 771 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Arg Thr Ser Pro Arg Arg Pro Leu Ile Leu Lys Arg Arg Arg Leu
 1               5                  10                  15

Pro Leu Pro Ile Gln Asn Ala Pro Ser Glu Thr Ser Glu Glu Glu Ala
            20                  25                  30

Lys Arg Ser Pro Gly Gln Gln Glu Pro Thr Gln Ala Gln Ala Ser Gln
        35                  40                  45

Asp Val Ala Glu Ser Ser Cys Lys Phe Pro Ala Gly Ile Lys Ile
    50                  55                  60

Ile Asn His Pro Thr Val Pro Asn Thr Gln Val Val Ala Ile Pro Asn
65                  70                  75                  80

Asn Ala Asp Ile Gln Ser Ile Ile Thr Ala Leu Thr Ala Lys Gly Lys
                85                  90                  95

Glu Ser Gly Ser Ser Gly Pro Asn Lys Phe Ile Leu Ile Ser Gly
            100                 105                 110

Gly Ala Ser Ser His Pro Pro Asp Pro Gln Ser Gln Ala Gln Thr Ser
        115                 120                 125

Thr Asp Ser Lys Arg Thr Glu Leu Ile Thr Glu Thr Leu Gly Pro Lys
    130                 135                 140

Pro Gly Ala Lys Gly Val Pro Val Pro Lys Pro Pro Gly Ala Leu Pro
145                 150                 155                 160

Arg Gln Arg Gln Glu Ser Cys Gly Gly Glu Ala Ala Gly Cys Thr Leu
                165                 170                 175

Asp Asn Ser Leu Thr Asn Ile Gln Trp Leu Gly Lys Met Ser Ser Asp
            180                 185                 190

Gly Leu Gly Arg Cys Ser Ile Lys Gln Glu Leu Glu Glu Lys Glu Asn
        195                 200                 205

Cys His Leu Glu Gln Asn Arg Val Lys Val Glu Ala Pro Ser Arg Ala
    210                 215                 220

Ser Val Ser Trp Gln Asp Ser Val Ser Glu Arg Pro Pro Tyr Ser Tyr
225                 230                 235                 240

Met Ala Met Ile Gln Phe Ala Ile Asn Ser Thr Glu Arg Lys Arg Met
                245                 250                 255

Thr Leu Lys Asp Ile Tyr Thr Trp Ile Glu Asp His Phe Pro Tyr Phe
            260                 265                 270
```

| | | | | | | | | | | | | | | |
|---|---|---|---|---|---|---|---|---|---|---|---|---|---|---|
| Lys | His | Ile 275 | Ala | Lys | Pro | Gly | Trp 280 | Lys | Cys | Trp | His 285 | Gln | Ala | Tyr | His |
| Lys | Leu 290 | Gly | Pro | Gln | Asn | Ser 295 | Ile | Arg | His | Asn 300 | Leu | Ser | Leu | His | Asp |
| Met 305 | Phe | Val | Arg | Glu | Thr 310 | Ser | Ala | Asn | Gly | Lys 315 | Val | Ser | Phe | Trp | Thr 320 |
| Ile | His | Pro | Ser | Ala 325 | Asn | Arg | Tyr | Leu | Thr 330 | Leu | Asp | Gln | Val | Phe 335 | Lys |
| Pro | Leu | Glu | Pro 340 | Gly | Ser | Pro | Gln | Ser 345 | Pro | Glu | His | Leu | Glu 350 | Ser | Gln |
| Gln | Lys | Arg 355 | Pro | Asn | Pro | Glu | Leu 360 | Arg | Arg | Asn | Val | Thr 365 | Ile | Lys | Thr |
| Glu | Leu 370 | Pro | Leu | Gly | Ala | Arg 375 | Arg | Lys | Met | Lys | Pro 380 | Leu | Leu | Pro | Arg |
| Val 385 | Ser | Ser | Tyr | Leu | Val 390 | Pro | Ile | Gln | Phe | Pro 395 | Val | Asn | Gln | Ser | Leu 400 |
| Val | Leu | Gln | Pro | Ser 405 | Val | Lys | Val | Pro | Leu 410 | Pro | Leu | Ala | Ala | Ser 415 | Leu |
| Met | Ser | Ser | Glu 420 | Leu | Ala | Arg | His | Ser 425 | Lys | Arg | Val | Arg | Ile 430 | Ala | Pro |
| Lys | Val | Leu 435 | Leu | Ser | Asn | Glu | Gly 440 | Ile | Ala | Pro | Leu | Pro 445 | Ala | Thr | Glu |
| Pro | Met 450 | Lys | Glu | Glu | Lys | Pro 455 | Leu | Leu | Gly | Glu | Gly 460 | Leu | Leu | Pro | Leu |
| Leu 465 | Pro | Ile | Gln | Ser | Ile 470 | Lys | Glu | Glu | Val | Ile 475 | Gln | Pro | Gly | Glu | Asp 480 |
| Ile | Pro | His | Leu | Glu 485 | Arg | Pro | Ile | Lys | Val 490 | Glu | Ser | Pro | Pro | Leu 495 | Glu |
| Glu | Trp | Pro | Ser 500 | Pro | Cys | Ala | Ser | Val 505 | Lys | Glu | Glu | Leu | Ser 510 | Asn | Ser |
| Trp | Glu | Asp 515 | Ser | Ser | Cys | Ser | Pro 520 | Thr | Pro | Lys | Pro | Lys 525 | Ser | Ser | Tyr |
| Cys | Gly 530 | Leu | Lys | Ser | Pro | Thr 535 | Arg | Cys | Val | Ser | Glu 540 | Met | Leu | Val | Thr |
| Lys 545 | Arg | Arg | Glu | Lys | Arg 550 | Glu | Val | Ser | Arg | Arg 555 | Arg | Lys | Gln | His 560 |
| Leu | Gln | Pro | Pro | Cys 565 | Leu | Asp | Glu | Pro | Glu 570 | Leu | Phe | Phe | Ser | Glu 575 | Asp |
| Ser | Ser | Thr | Phe 580 | Arg | Pro | Ala | Met | Glu 585 | Ile | Leu | Ala | Glu | Ser 590 | Ser | Glu |
| Pro | Ala | Pro 595 | Gln | Leu | Ser | Cys | Pro 600 | Gln | Glu | Glu | Gly | Gly 605 | Pro | Phe | Lys |
| Thr | Pro 610 | Ile | Lys | Glu | Thr | Leu 615 | Pro | Val | Ser | Ser | Thr 620 | Pro | Ser | Lys | Ser |
| Val 625 | Leu | Ser | Arg | Asp | Pro 630 | Glu | Ser | Trp | Arg | Leu 635 | Thr | Pro | Pro | Ala | Lys 640 |
| Val | Gly | Gly | Leu | Asp 645 | Phe | Ser | Pro | Val | Arg 650 | Thr | Pro | Gln | Gly | Ala 655 | Phe |
| Gly | Pro | Leu | Pro 660 | Asp | Ser | Leu | Gly | Leu 665 | Met | Glu | Leu | Asn | Thr 670 | Thr | Pro |
| Leu | Lys | Ser 675 | Val | Pro | Leu | Phe | Asp 680 | Ser | Pro | Arg | Glu | Leu 685 | Leu | Asn | Ser |
| Glu | Ala | Phe | Asp | Leu | Ala | Ser | Asp | Pro | Phe | Ser | Ser | Pro | Pro | Pro |

|         |         |         |         | 690     |         |         |         |         | 695     |         |         |         |         | 700     |
|---------|---------|---------|---------|---------|---------|---------|---------|---------|---------|---------|---------|---------|---------|---------|
| His     | Leu     | Glu     | Ala     | Lys     | Pro     | Gly     | Ser     | Pro     | Glu     | Leu     | Gln     | Val     | Pro     | Ser     | Leu
| 705     |         |         |         |         | 710     |         |         |         |         | 715     |         |         |         |         | 720
| Ser     | Ala     | Asn     | Arg     | Ser     | Leu     | Thr     | Glu     | Gly     | Leu     | Val     | Leu     | Asp     | Thr     | Met     | Asn
|         |         |         |         | 725     |         |         |         |         | 730     |         |         |         |         | 735     |
| Asp     | Ser     | Leu     | Ser     | Lys     | Ile     | Leu     | Leu     | Asp     | Ile     | Ser     | Phe     | Pro     | Gly     | Leu     | Glu
|         |         |         |         | 740     |         |         |         |         | 745     |         |         |         |         | 750     |
| Glu     | Asp     | Pro     | Leu     | Gly     | Pro     | Asp     | Asn     | Ile     | Asn     | Trp     | Ser     | Gln     | Phe     | Ile     | Pro
|         |         |         | 755     |         |         |         |         | 760     |         |         |         |         | 765     |         |
| Glu     | Leu     | Arg     |         |         |         |         |         |         |         |         |         |         |         |         |
|         |         | 770     |         |         |         |         |         |         |         |         |         |         |         |         |

( 2 ) INFORMATION FOR SEQ ID NO:3:

( i ) SEQUENCE CHARACTERISTICS:
    ( A ) LENGTH: 3342 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: CDS
    ( B ) LOCATION: 70..2358

( x i ) SEQUENCE DESCRIPTION: SEQ ID NO:3:

| CGGCGGCGAC | TGCAGTCTGG | AGGGTCCACA | CTTGTGATTC | TCAATGGAGA | GTGAAAACGC | 60   |
| AGATTCATAA | TGAAAGCTAG | CCCCCGTCGG | CCACTGATTC | TCAAAAGACG | GAGGCTGCCC | 120  |
| CTTCCTGTTC | AAAATGCCCC | AAGTGAAACA | TCAGAGGAGG | AACCTAAGAG | ATCCCCTGCC | 180  |
| CAACAGGAGT | CTAATCAAGC | AGAGGCCTCC | AAGGAAGTGG | CGGAGTCCAA | CTCTTGCAAG | 240  |
| TTTCCAGCTG | GGATCAAGAT | TATTAACCAC | CCCACCATGC | CAACACGCA  | AGTAGTGGCC | 300  |
| ATCCCCAACA | ATGCTAATAT | TCACAGCATC | ATCACAGCAC | TGACTGCCAA | GGGAAAAGAG | 360  |
| AGTGGCAGTA | GTGGGCCCAA | CAAATTCATC | CTCATCAGCT | GTGGGGGAGC | CCCAACTCAG | 420  |
| CCTCCAGGAC | TCCGGCCTCA | AACCCAAACC | AGCTATGATG | CCAAAAGGAC | AGAAGTGACC | 480  |
| CTGGAGACCT | TGGGACCAAA | ACCTGCAGCT | AGGGATGTGA | ATCTTCCTAG | ACCACCTGGA | 540  |
| GCCCTTTGCG | AGCAGAAACG | GGAGACCTGT | GCAGATGGTG | AGGCAGCAGG | CTGCACTATC | 600  |
| AACAATAGCC | TATCCAACAT | CCAGTGGCTT | CGAAAGATGA | GTTCTGATGG | ACTGGGCTCC | 660  |
| CGCAGCATCA | AGCAAGAGAT | GGAGGAAAAG | GAGAATTGTC | ACCTGGAGCA | GCGACAGGTT | 720  |
| AAGGTTGAGG | AGCCTTCGAG | ACCATCAGCG | TCCTGGCAGA | ACTCTGTGTC | TGAGCGGCCA | 780  |
| CCCTACTCTT | ACATGGCCAT | GATACAATTC | GCCATCAACA | GCACTGAGAG | GAAGCGCATG | 840  |
| ACTTTGAAAG | ACATCTATAC | GTGGATTGAG | GACCACTTTC | CCTACTTTAA | GCACATTGCC | 900  |
| AAGCCAGGCT | GGAAGAACTC | CATCCGCCAC | AACCTTTCCC | TGCACGACAT | GTTTGTCCGG | 960  |
| GAGACGTCTG | CCAATGGCAA | GGTCTCCTTC | TGGACCATTC | ACCCAGTGC  | CAACCGCTAC | 1020 |
| TTGACATTGG | ACCAGGTGTT | TAAGCCACTG | GACCCAGGGT | CTCCACAATT | GCCCGAGCAC | 1080 |
| TTGGAATCAC | AGCAGAAACG | ACCGAATCCA | GAGCTCCGCC | GGAACATGAC | CATCAAAACC | 1140 |
| GAACTCCCCC | TGGGCGCACG | GCGGAAGATG | AAGCCACTGC | TACCACGGGT | CAGCTCATAC | 1200 |
| CTGGTACCTA | TCCAGTTCCC | GGTGAACCAG | TCACTGGTGT | TGCAGCCCTC | GGTGAAGGTG | 1260 |
| CCATTGCCCC | TGGCGGCTTC | CCTCATGAGC | TCAGAGCTTG | CCCGCCATAG | CAAGCGAGTC | 1320 |
| CGCATTGCCC | CCAAGGTGCT | GCTAGCTGAG | GAGGGGATAG | CTCCTCTTTC | TTCTGCAGGA | 1380 |

| | | | | | | |
|---|---|---|---|---|---|---|
| CCAGGGAAAG | AGGAGAAACT | CCTGTTTGGA | GAAGGGTTTT | CTCCTTTGCT | TCCAGTTCAG | 1440 |
| ACTATCAAGG | AGGAAGAAAT | CCAGCCTGGG | GAGGAAATGC | CACACTTAGC | GAGACCCATC | 1500 |
| AAAGTGGAGA | GCCCTCCCTT | GGAAGAGTGG | CCCTCCCCGG | CCCCATCTTT | CAAAGAGGAA | 1560 |
| TCATCTCACT | CCTGGGAGGA | TTCGTCCCAA | TCTCCACCC | CAAGACCCAA | GAAGTCCTAC | 1620 |
| AGTGGGCTTA | GGTCCCCAAC | CCGGTGTGTC | TCGGAAATGC | TTGTGATTCA | ACACAGGGAG | 1680 |
| AGGAGGGAGA | GGAGCCGGTC | TCGGAGGAAA | CAGCATCTAC | TGCCTCCCTG | TGTGGATGAG | 1740 |
| CCGGAGCTGC | TCTTCTCAGA | GGGGCCCAGT | ACTTCCGCT | GGGCCGCAGA | GCTCCGTTC | 1800 |
| CCAGCAGACT | CCTCTGACCC | TGCCTCCCAG | CTCAGCTACT | CCCAGGAAGT | GGGAGGACCT | 1860 |
| TTTAAGACAC | CCATTAAGGA | AACGCTGCCC | ATCTCCTCCA | CCCCGAGCAA | ATCTGTCCTC | 1920 |
| CCCAGAACCC | CTGAATCCTG | GAGGCTCACG | CCCCCAGCCA | AAGTAGGGGG | ACTGGATTTC | 1980 |
| AGCCAGTAC | AAACCTCCCA | GGGTGCCTCT | GACCCCTTGC | CTGACCCCT | GGGGCTGATG | 2040 |
| GATCTCAGCA | CCACTCCCTT | GCAAAGTGCT | CCCCCCCTTG | AATCACCGCA | AAGGCTCCTC | 2100 |
| AGTTCAGAAC | CCTTAGACCT | CATCTCCGTC | CCCTTTGGCA | ACTCTTCTCC | CTCAGATATA | 2160 |
| GACGTCCCCA | AGCCAGGCTC | CCCGGAGCCA | CAGGTTTCTG | GCCTTGCAGC | CAATCGTTCT | 2220 |
| CTGACAGAAG | GCCTGGTCCT | GGACACAATG | AATGACAGCC | TCAGCAAGAT | CCTGCTGGAC | 2280 |
| ATCAGCTTTC | CTGGCCTGGA | CGAGGACCCA | CTGGGCCCTG | ACAACATCAA | CTGGTCCCAG | 2340 |
| TTTATTCCTG | AGCTACAGTA | GAGCCCTGCC | CTTGCCCCTG | TGCTCAAGCT | GTCCACCATC | 2400 |
| CCGGGCACTC | CAAGGCTCAG | TGCACCCCAA | GCCTCTGAGT | GAGGACAGCA | GGCAGGGACT | 2460 |
| GTTCTGCTCC | TCATAGCTCC | CTGCTGCCTG | ATTATGCAAA | AGTAGCAGTC | ACACCCTAGC | 2520 |
| CACTGCTGGG | ACCTTGTGTT | CCCCAAGAGT | ATCTGATTCC | TCTGCTGTCC | CTGCCAGGAG | 2580 |
| CTGAAGGGTG | GGAACAACAA | AGGCAATGGT | GAAAAGAGAT | TAGGAACCCC | CCAGCCTGTT | 2640 |
| TCCATTCTCT | GCCCAGCAGT | CTCTTACCTT | CCCTGATCTT | TGCAGGGTGG | TCCGTGTAAA | 2700 |
| TAGTATAAAT | TCTCCAAATT | ATCCTCTAAT | TATAAATGTA | AGCTTATTTC | CTTAGATCAT | 2760 |
| TATCCAGAGA | CTGCCAGAAG | GTGGGTAGGA | TGACCTGGGG | TTTCAATTGA | CTTCTGTTCC | 2820 |
| TTGCTTTTAG | TTTTGATAGA | AGGGAAGACC | TGCAGTGCAC | GGTTTCTTCC | AGGCTGAGGT | 2880 |
| ACCTGGATCT | TGGGTTCTTC | ACTGCAGGGA | CCCAGACAAG | TGGATCTGCT | TGCCAGAGTC | 2940 |
| CTTTTTGCCC | CTCCCTGCCA | CCTCCCCGTG | TTTCCAAGTC | AGCTTTCCTG | CAAGAAGAAA | 3000 |
| TCCTGGTTAA | AAAAGTCTTT | TGTATTGGGT | CAGGAGTTGA | ATTTGGGGTG | GGAGGATGGA | 3060 |
| TGCAACTGAA | GCAGAGTGTG | GGTGCCCAGA | TGTGCGCTAT | TAGATGTTTC | TCTGATAATG | 3120 |
| TCCCCAATCA | TACCAGGGAG | ACTGGCATTG | ACGAGAACTC | AGGTGGAGGC | TTGAGAAGGC | 3180 |
| CGAAAGGGCC | CCTGACCTGC | CTGGCTTCCT | TAGCTTGCCC | CTCAGCTTTG | CAAAGAGCCA | 3240 |
| CCCTAGGCCC | CAGCTGACCG | CATGGGTGTG | AGCCAGCTTG | AGAACACTAA | CTACTCAATA | 3300 |
| AAAGCGAAGG | TGGACCNAAA | AAAAAAAAA | AAAAAACTCG | AG | | 3342 |

( 2 ) INFORMATION FOR SEQ ID NO:4:

( i ) SEQUENCE CHARACTERISTICS:
        ( A ) LENGTH: 763 amino acids
        ( B ) TYPE: amino acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 70..2358

( x i ) SEQUENCE DESCRIPTION: SEQ ID NO:4:

| | | | | | | | | | | | | | | |
|---|---|---|---|---|---|---|---|---|---|---|---|---|---|---|
| Met | Lys | Ala | Ser | Pro | Arg | Arg | Pro | Leu | Ile | Leu | Lys | Arg | Arg | Leu |
| 1 | | | | 5 | | | | | 10 | | | | | 15 |
| Pro | Leu | Pro | Val | Gln | Asn | Ala | Pro | Ser | Glu | Thr | Ser | Glu | Glu | Pro |
| | | | 20 | | | | | 25 | | | | | 30 | |
| Lys | Arg | Ser | Pro | Ala | Gln | Gln | Glu | Ser | Asn | Gln | Ala | Glu | Ala | Ser | Lys |
| | | 35 | | | | | 40 | | | | | 45 | | |
| Glu | Val | Ala | Glu | Ser | Asn | Ser | Cys | Lys | Phe | Pro | Ala | Gly | Ile | Lys | Ile |
| | 50 | | | | | 55 | | | | | 60 | | | | |
| Ile | Asn | His | Pro | Thr | Met | Pro | Asn | Thr | Gln | Val | Val | Ala | Ile | Pro | Asn |
| 65 | | | | | 70 | | | | 75 | | | | | | 80 |
| Asn | Ala | Asn | Ile | His | Ser | Ile | Ile | Thr | Ala | Leu | Thr | Ala | Lys | Gly | Lys |
| | | | | 85 | | | | | 90 | | | | | 95 | |
| Glu | Ser | Gly | Ser | Ser | Gly | Pro | Asn | Lys | Phe | Ile | Leu | Ile | Ser | Cys | Gly |
| | | | 100 | | | | | 105 | | | | | 110 | | |
| Gly | Ala | Pro | Thr | Gln | Pro | Pro | Gly | Leu | Arg | Pro | Gln | Thr | Gln | Thr | Ser |
| | | 115 | | | | | 120 | | | | | 125 | | | |
| Tyr | Asp | Ala | Lys | Arg | Thr | Glu | Val | Thr | Leu | Glu | Thr | Leu | Gly | Pro | Lys |
| | 130 | | | | | 135 | | | | | 140 | | | | |
| Pro | Ala | Ala | Arg | Asp | Val | Asn | Leu | Pro | Arg | Pro | Pro | Gly | Ala | Leu | Cys |
| 145 | | | | | 150 | | | | | 155 | | | | | 160 |
| Glu | Gln | Lys | Arg | Glu | Thr | Cys | Ala | Asp | Gly | Glu | Ala | Ala | Gly | Cys | Thr |
| | | | | 165 | | | | | 170 | | | | | 175 | |
| Ile | Asn | Asn | Ser | Leu | Ser | Asn | Ile | Gln | Trp | Leu | Arg | Lys | Met | Ser | Ser |
| | | | 180 | | | | | 185 | | | | | 190 | | |
| Asp | Gly | Leu | Gly | Ser | Arg | Ser | Ile | Lys | Gln | Glu | Met | Glu | Glu | Lys | Glu |
| | | 195 | | | | | 200 | | | | | 205 | | | |
| Asn | Cys | His | Leu | Glu | Gln | Arg | Gln | Val | Lys | Val | Glu | Glu | Pro | Ser | Arg |
| | 210 | | | | | 215 | | | | | 220 | | | | |
| Pro | Ser | Ala | Ser | Trp | Gln | Asn | Ser | Val | Ser | Glu | Arg | Pro | Pro | Tyr | Ser |
| 225 | | | | | 230 | | | | | 235 | | | | | 240 |
| Tyr | Met | Ala | Met | Ile | Gln | Phe | Ala | Ile | Asn | Ser | Thr | Glu | Arg | Lys | Arg |
| | | | | 245 | | | | | 250 | | | | | 255 | |
| Met | Thr | Leu | Lys | Asp | Ile | Tyr | Thr | Trp | Ile | Glu | Asp | His | Phe | Pro | Tyr |
| | | | 260 | | | | | 265 | | | | | 270 | | |
| Phe | Lys | His | Ile | Ala | Lys | Pro | Gly | Trp | Lys | Asn | Ser | Ile | Arg | His | Asn |
| | | 275 | | | | | 280 | | | | | 285 | | | |
| Leu | Ser | Leu | His | Asp | Met | Phe | Val | Arg | Glu | Thr | Ser | Ala | Asn | Gly | Lys |
| | 290 | | | | | 295 | | | | | 300 | | | | |
| Val | Ser | Phe | Trp | Thr | Ile | His | Pro | Ser | Ala | Asn | Arg | Tyr | Leu | Thr | Leu |
| 305 | | | | | 310 | | | | | 315 | | | | | 320 |
| Asp | Gln | Val | Phe | Lys | Pro | Leu | Asp | Pro | Gly | Ser | Pro | Gln | Leu | Pro | Glu |
| | | | | 325 | | | | | 330 | | | | | 335 | |
| His | Leu | Glu | Ser | Gln | Gln | Lys | Arg | Pro | Asn | Pro | Glu | Leu | Arg | Arg | Asn |
| | | | 340 | | | | | 345 | | | | | 350 | | |
| Met | Thr | Ile | Lys | Thr | Glu | Leu | Pro | Leu | Gly | Ala | Arg | Arg | Lys | Met | Lys |
| | | | 355 | | | | | 360 | | | | | 365 | | |
| Pro | Leu | Leu | Pro | Arg | Val | Ser | Ser | Tyr | Leu | Val | Pro | Ile | Gln | Phe | Pro |
| | | 370 | | | | | 375 | | | | | 380 | | | |
| Val | Asn | Gln | Ser | Leu | Val | Leu | Gln | Pro | Ser | Val | Lys | Val | Pro | Leu | Pro |
| 385 | | | | | 390 | | | | | 395 | | | | | 400 |
| Leu | Ala | Ala | Ser | Leu | Met | Ser | Ser | Glu | Leu | Ala | Arg | His | Ser | Lys | Arg |
| | | | | 405 | | | | | 410 | | | | | 415 | |

|  |  |  |  |  |  |  |  |  |  |  |  |  |  |  |
|--|--|--|--|--|--|--|--|--|--|--|--|--|--|--|
| Val | Arg | Ile | Ala<br>420 | Pro | Lys | Val | Leu<br>425 | Leu | Ala | Glu | Glu | Gly | Ile<br>430 | Ala | Pro |
| Leu | Ser | Ser<br>435 | Ala | Gly | Pro | Gly | Lys<br>440 | Glu | Glu | Lys | Leu | Leu<br>445 | Phe | Gly | Glu |
| Gly | Phe<br>450 | Ser | Pro | Leu | Leu | Pro<br>455 | Val | Gln | Thr | Ile | Lys<br>460 | Glu | Glu | Glu | Ile |
| Gln<br>465 | Pro | Gly | Glu | Glu | Met<br>470 | Pro | His | Leu | Ala | Arg<br>475 | Pro | Ile | Lys | Val | Glu<br>480 |
| Ser | Pro | Pro | Leu | Glu<br>485 | Glu | Trp | Pro | Ser | Pro<br>490 | Ala | Pro | Ser | Phe | Lys<br>495 | Glu |
| Glu | Ser | Ser | His<br>500 | Ser | Trp | Glu | Asp | Ser<br>505 | Ser | Gln | Ser | Pro | Thr<br>510 | Pro | Arg |
| Pro | Lys | Lys<br>515 | Ser | Tyr | Ser | Gly | Leu<br>520 | Arg | Ser | Pro | Thr | Arg<br>525 | Cys | Val | Ser |
| Glu | Met<br>530 | Leu | Val | Ile | Gln | His<br>535 | Arg | Glu | Arg | Arg | Glu<br>540 | Arg | Ser | Arg | Ser |
| Arg<br>545 | Arg | Lys | Gln | His | Leu<br>550 | Leu | Pro | Pro | Cys | Val<br>555 | Asp | Glu | Pro | Glu | Leu<br>560 |
| Leu | Phe | Ser | Glu | Gly<br>565 | Pro | Ser | Thr | Ser | Arg<br>570 | Trp | Ala | Ala | Glu | Leu<br>575 | Pro |
| Phe | Pro | Ala | Asp<br>580 | Ser | Ser | Asp | Pro | Ala<br>585 | Ser | Gln | Leu | Ser | Tyr<br>590 | Ser | Gln |
| Glu | Val | Gly<br>595 | Gly | Pro | Phe | Lys | Thr<br>600 | Pro | Ile | Lys | Glu | Thr<br>605 | Leu | Pro | Ile |
| Ser | Ser<br>610 | Thr | Pro | Ser | Lys | Ser<br>615 | Val | Leu | Pro | Arg | Thr<br>620 | Pro | Glu | Ser | Trp |
| Arg<br>625 | Leu | Thr | Pro | Pro | Ala<br>630 | Lys | Val | Gly | Gly | Leu<br>635 | Asp | Phe | Ser | Pro | Val<br>640 |
| Gln | Thr | Ser | Gln | Gly<br>645 | Ala | Ser | Asp | Pro | Leu<br>650 | Pro | Asp | Pro | Leu | Gly<br>655 | Leu |
| Met | Asp | Leu | Ser<br>660 | Thr | Thr | Pro | Leu | Gln<br>665 | Ser | Ala | Pro | Pro | Leu<br>670 | Glu | Ser |
| Pro | Gln | Arg<br>675 | Leu | Leu | Ser | Ser | Glu<br>680 | Pro | Leu | Asp | Leu | Ile<br>685 | Ser | Val | Pro |
| Phe | Gly<br>690 | Asn | Ser | Ser | Pro | Ser<br>695 | Asp | Ile | Asp | Val | Pro<br>700 | Lys | Pro | Gly | Ser |
| Pro<br>705 | Glu | Pro | Gln | Val | Ser<br>710 | Gly | Leu | Ala | Ala | Asn<br>715 | Arg | Ser | Leu | Thr | Glu<br>720 |
| Gly | Leu | Val | Leu | Asp<br>725 | Thr | Met | Asn | Asp | Ser<br>730 | Leu | Ser | Lys | Ile | Leu<br>735 | Leu |
| Asp | Ile | Ser | Phe<br>740 | Pro | Gly | Leu | Asp | Glu<br>745 | Asp | Pro | Leu | Gly | Pro<br>750 | Asp | Asn |
| Ile | Asn | Trp<br>755 | Ser | Gln | Phe | Ile | Pro<br>760 | Glu | Leu | Gln |  |  |  |  |  |

What is claimed is:

1. An isolated DNA sequence encoding a hepatocyte nuclear factor-3δ (HNF3δ) protein, which DNA sequence comprises a DNA sequence selected from the group consisting of:

(a) nucleotides #1 or #88 to #2400 or #3441 of SEQ ID NO: 1;

(b) nucleotides #1 or #70 to #2358 or #3342 of SEQ ID NO: 3; and (c) nucleotide sequences which hybridize to (a) or (b) under stringent hybridization conditions and encode a protein which exhibits a HNF3δ activity, wherein stringent hybridization conditions are 15mM sodium chloride, 1.5mM sodium citrate pH 7.0, 0.1% sodium dodecyl sulfate and 65° C.

2. A vector comprising the isolated DNA sequence of claim 1 in operative association with an expression control sequence.

3. A host cell transformed with the vector of claim 2.

4. A method for producing purified HNF3δ protein, said method comprising the steps of:

(a) culturing a host cell transformed with the isolated DNA sequence according to claim 1; and (b) recovering and purifying said HNF3δ protein from the culture medium.

5. A chimeric DNA molecule comprising the isolated DNA sequence according to claim 1, linked to a heterologous promoter sequence.

6. An isolated DNA sequence encoding a HNF3δ protein, which DNA sequence comprises a DNA sequence selected from the group consisting of:

(a) a nucleotide sequence encoding amino acids #1 to #771 of SEQ ID NO: 2;

(b) a nucleotide sequence encoding amino acids #1 to #763 of SEQ ID NO: 4; and (c) a nucleotide sequence which hybridizes to (a) or (b) under stringent hybridization conditions and encode a protein which exhibits a HNF3δ activity, wherein stringent hybridization conditions are 15mM sodium chloride, 1.5mM sodium citrate pH 7.0, 0.1% sodium dodecyl sulfate and 65° C.

7. A vector comprising the isolated DNA sequence of claim 6 in operative association with an expression control sequence.

8. A host cell transformed with the vector of claim 7.

9. A method for producing purified HNF3δ protein, said method comprising the steps of:

(a) culturing a host cell transformed with the isolated DNA sequence according to claim 6; and (b) recovering and purifying said HNF3δ protein from the culture medium.

10. An isolated DNA molecule having a sequence encoding a protein which exhibits a HNF3δ activity, said DNA molecule comprising a DNA sequence selected from the group consisting of:

(a) nucleotide #88 to #2400 of SEQ ID NO: 1;

(b) nucleotide #70 to #2358 of SEQ ID NO: 3; and (c) DNA sequences which encode the same protein as that encoded by (a) or (b).

11. A vector comprising the DNA molecule of claim 10 in operative association with an expression control sequence.

12. A host cell transformed with the vector of claim 11.

13. The isolated DNA molecule according to claim 10, said DNA molecule comprising nucleotide #70 to #2358 of SEQ ID NO. 3.

14. A vector comprising the DNA molecule of claim 13 in operative association with an expression control sequence.

15. A host cell transformed with the vector of claim 14.

16. A method for producing purified HNF3δ protein, said method comprising the steps of:

(a) culturing a host cell transformed with the isolated DNA molecule according to claim 10; and (b) recovering and purifying said HNF3δ protein from the culture medium.

17. An isolated DNA plasmid which has been deposited with the American Type Culture Collection under Depository Access Number ATCC 97704.

18. An isolated DNA plasmid which has been deposited with the American Type Culture Collection under Depository Access Number ATCC 97705.

* * * * *